United States Patent [19]
Wilk

[11] Patent Number: 5,318,519
[45] Date of Patent: Jun. 7, 1994

[54] METHOD AND APPARATUS FOR SUPPLYING NUTRITION

[76] Inventor: Peter J. Wilk, 185 W. End Ave., New York, N.Y. 10023

[21] Appl. No.: 932,368

[22] Filed: Aug. 19, 1992

[51] Int. Cl.$^5$ ............................................. A61M 5/00
[52] U.S. Cl. ..................................... 604/52; 604/151; 604/891.1; 128/899
[58] Field of Search ..................... 604/49, 50, 52, 53, 604/65, 93, 151, 175, 891.1; 128/899, DIG. 12

[56] References Cited

U.S. PATENT DOCUMENTS

| | | | |
|---|---|---|---|
| 4,315,513 | 2/1982 | Nawash et al. | 604/175 |
| 4,335,711 | 6/1982 | Olson | 604/83 |
| 4,344,435 | 8/1982 | Aubin | 604/175 |
| 4,525,165 | 6/1985 | Fischell | 604/891.1 |
| 4,596,575 | 6/1986 | Rosenberg et al. | 604/891.1 |
| 4,687,468 | 8/1987 | Gianturco | 604/9 |
| 4,822,337 | 4/1989 | Newhouse et al. | 604/50 |
| 4,826,810 | 5/1989 | Aoki | 604/151 |
| 4,911,168 | 3/1990 | Davis | 604/50 |
| 5,069,662 | 12/1991 | Bodden | 604/4 |
| 5,217,460 | 6/1993 | Knoepfler | 606/205 |

Primary Examiner—Ralph Lewis
Attorney, Agent, or Firm—R. Neil Sudol; Henry D. Coleman

[57] ABSTRACT

A medical method for providing nutrition to a patient comprises the steps of providing a container having an inlet, an outlet and a pump at the outlet and surgically inserting the container into the abdominal cavity. The container outlet is surgically connected to a selected vein in the portal vein system so that the container communicates with the liver via the container outlet and the selected vein of the portal vein system. The pump is then operated to move a liquid nutritive composition from the container to the selected vein in the portal vein system.

9 Claims, 1 Drawing Sheet

METHOD AND APPARATUS FOR SUPPLYING NUTRITION

BACKGROUND OF THE INVENTION

This invention relates to a method for supplying nutrition. More particularly, this invention relates to a method for total parenteral nutrition. This invention also relates to an apparatus for use in implementing the method.

A significant number of ailing individuals are unable to obtain nutrition through the normal channels, namely, through the mouth and the gastrointestinal tract. Such individuals are provided periodically with a liquid nutritive composition from a reservoir or supply which may be provided on a stand or attached to the person, e.g., on a belt or on a back harnass. A tube or central intravenous line extends from the reservoir to a vein in the person's chest. The nutritive composition then moves to the heart and through the body until it is eventually absorbed.

This conventional technique for providing liquid nutrition is sometimes intolerably inconvenient. The patient is saddled with a bag or container which is uncomfortable and embarassing in some situations. Alternatively, the patient must be connected to a supply of liquid nutrition by a health professional. This latter method is especially undesirable in that the freedom of the individual is restricted.

OBJECTS OF THE INVENTION

An object of the present invention is to provide a new method for providing intravenous nutrition to a person.

Another object of the present invention is to provide such a method which is less degrading and more convenient than conventional techniques.

Another, more particular, object of the present invention is to provide a method for providing total parenteral nutrition.

A further particular object of the present invention is to provide a device or apparatus for carrying out the method.

Yet another particular object of the present invention is to provide such an apparatus which is easy to manufacture and reliable.

These and other objects of the present invention will be apparent from the drawings and detailed descriptions herein.

SUMMARY OF THE INVENTION

A medical method for providing nutrition to a patient comprises, in accordance with the present invention, the steps of (a) providing a container having an inlet, an outlet and a pump at the outlet, (b) surgically inserting the container into the abdominal cavity, (c) surgically connecting the outlet to a selected vein in the portal vein system so that the container communicates with the liver via the container outlet and the selected vein of the portal vein system, and (d) operating the pump to move a liquid nutritive composition from the container to the selected vein in the portal vein system.

Pursuant to another feature of the present invention, the method further comprises the steps of (e) providing a port in an abdominal wall of the patient and (f) connecting the container inlet to the port. In this event, the method may also comprise the step of feeding a supply of liquid nutrient to the abdominally implanted container via the port in the abdominal wall and the container inlet.

Where the container is provided with a power source for energizing the pump, the method further comprises the step of charging the power source from a power supply outside the patient's body. The energization of the power source may be effectuated by connecting the power source to the power supply via a lead extending through the abdominal wall of the patient. Alternatively, the pump may be connected to a wireless energy receiver attached to the implanted abdominal container. The receiver may extract power transmitted, for example, via radio waves from an external power source.

Pursuant to another feature of the present invention, the inserting of the abdominal container or reservoir includes the step of disposing the container to rest on the pelvic rim.

A related method for obtaining nutrition comprises, in accordance with the present invention, the steps of (i) connecting, to a port provided in a person's abdominal wall, a supply of a liquid nutrient, (ii) moving the liquid nutrient from the external supply through the port and through an inlet supply line in the person's abdomen to a surgically implanted abdominal reservoir, (iii) disconnecting the supply from the port, (iv) closing the port upon disconnection of the supply therefrom, and (v) automatically pumping an amount of the nutrient from the reservoir to a vein of the portal vein system.

An apparatus for supplying total parenteral nutrition to a person comprises, in accordance with the present invention, a container having an inlet port and an outlet port, a port component disposable in the person's abdominal wall. A first tube or conduit is provided for connecting the container inlet port to the port component in the abdominal wall. A second tube or conduit is provided for connecting the container outlet port to a selected vein of the portal vein system of the person. A pump is mounted to the container and is in operative contact with either the container and/or the outlet conduit to periodically pump an aliquot of a liquid nutrient from the container to the selected vein of the portal vein system.

Where the pump includes a power source, a lead or a wireless power receiver is operatively connected to the power source for enabling a periodic recharging of the power source.

A method for providing intravenous nutrition to a person is less degrading and more convenient than conventional techniques, at least to some patients. The method provides total parenteral nutrition without the necessity for carrying around an external reservoir or supply.

DETAILED DESCRIPTION

Figure 1:
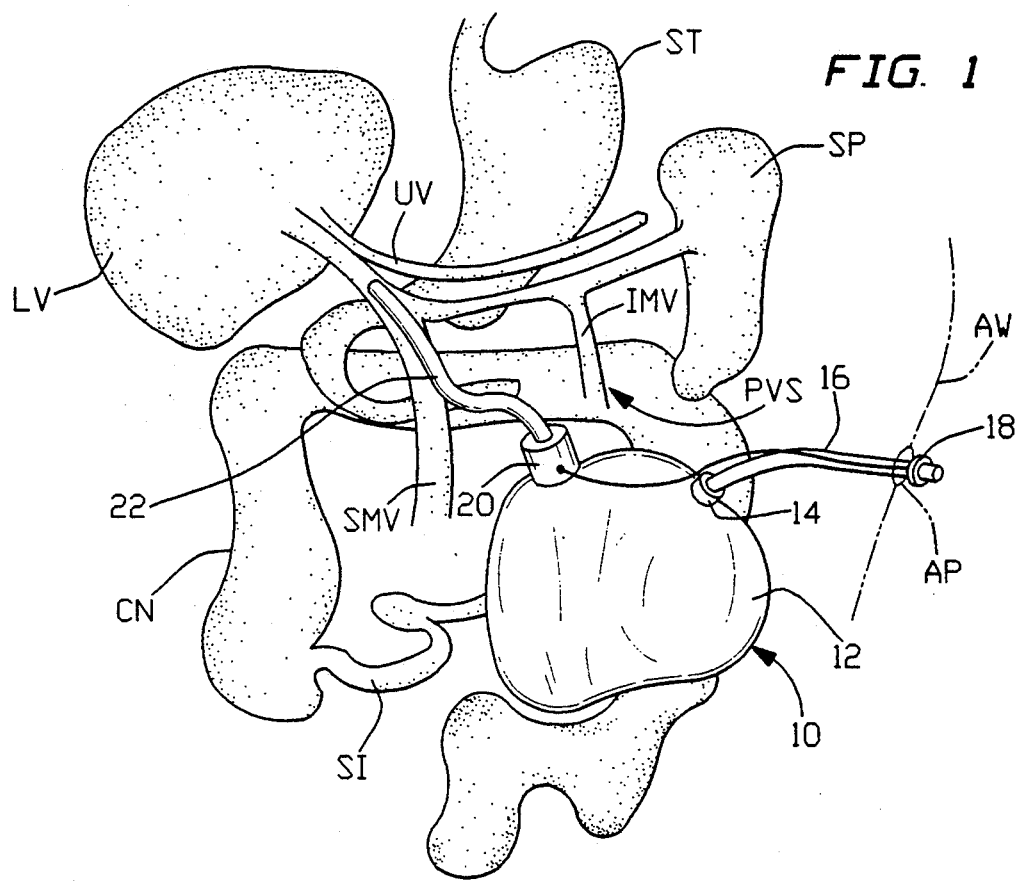
FIG. 1 is a diagram of abdominal organs of a patient, schematically showing an implanted nutrition reservoir assembly in accordance with the present invention.

As illustrated in FIG. 1, an individual's abdominal organs include the stomach ST, the liver LV, the spleen SP, the colon CN, the small intestine SI and the portal vein system PVS. The portal vein system PVS includes blood vessels which extend from the intestines CN and SI to the liver for delivering thereto nutrient carrying blood for processing by the liver LV. The portal vein system PVS includes the superior mesenteric vein SMV, the inferior mesenteric vein IMV, the spleen vein SV and the umbilical vein UV.

As further illustrated in FIG. 1, an assembly 10 for supplying total parenteral nutrition has been surgically implanted into the abdomen. The nutrition assembly 10 basically comprises a reservoir or container 12 which is implanted to rest on the pelvic rim PR.

Container 12 has an inlet port 14 which is surgically connected via a tube or conduit 16 to a port component 18 disposed in the abdominal wall AW of the patient. A pump 20 is mounted to container 12 at an outlet thereof. A tube or outlet conduit 22 extends from pump 20 to the superior mesenteric vein SMV where the distal end of the outlet conduit has been surgically inserted.

It is to be noted that outlet conduit 16 may be connected at its distal end to virtually any vein of the portal vein system, including, but not limited, to the superior mesenteric vein, the inferior mesenteric vein and the spleen vein.

Container 12 holds a supply of a liquid nutritive solution for feeding by pump 20 directly into the portal vein system and from thence to the liver. The feeding of the liquid nourishment to the portal vein system is considered more efficient than the conventional feeding to a vein in the chest inasmuch as nutritive substances need not be carried around the body prior to extraction by the liver for processing.

Container 12 is surgically inserted into the abdominal cavity AC of the patient so that the container rests on pelvic rim PV. The disposition of container 12 may be effectuated through open surgery or laparoscopically. In the latter technique, container 12 must be of sufficient flexibility to permit collapse and folding into a configuration small enough to fit down a laparoscopic cannula or trocar sleeve. Upon insertion of the collapsed bag into the abdomen, the bag is opened and positioned, via the use of laparoscopic gaspers.

Container 12 is accordingly made of a flexible biocompatible material such as silicone or a nonbioabsorbable polymeric composition.

An outlet of container 12 (at pump 20) is surgically connected to a selected vein in the portal vein system PVS so that container 12 communicates with liver LV via the container outlet and the selected vein. The connection of outlet conduit 16 to the portal vein system PVS may be implemented after the disposition of container 12 in the abdomen. Alternatively, it is possible to connect conduit 16 first to the portal vein system and subsequently to container 12. In the latter event, it is particulary necessary to test the integrity of the connection of the conduit 16 to container 16, or to pump 20, to ensure that liquid nutrient does not leak into the abdomen. In fact, the entire parental nutrition system should be tested after installation to ensure the integrity of all lines and connections. During such testing, pump 20 is operated to move liquid nutrient from container 12 to the selected vein in the portal vein system PVS.

During the surgical implantation procedure, port component 18 is positioned in an aperture AP formed in the abdominal all AW and is connected to inlet port 14 via tube or conduit 16. Upon the disposition of container 12 in the abdomen and the connection of the container to port component 18 via inlet conduit 16, port component 18 may be connected to an external source of nutrient (not shown). The nutrient is fed from the external source to container 12 via port component 18, inlet conduit 16 and inlet port 14. This feeding, which may take place periodically after the completion of the operation in order to refill container or reservoir 14, should be tested prior to the completion of the implantation operation to ensure effective system operation.

Figure 2:
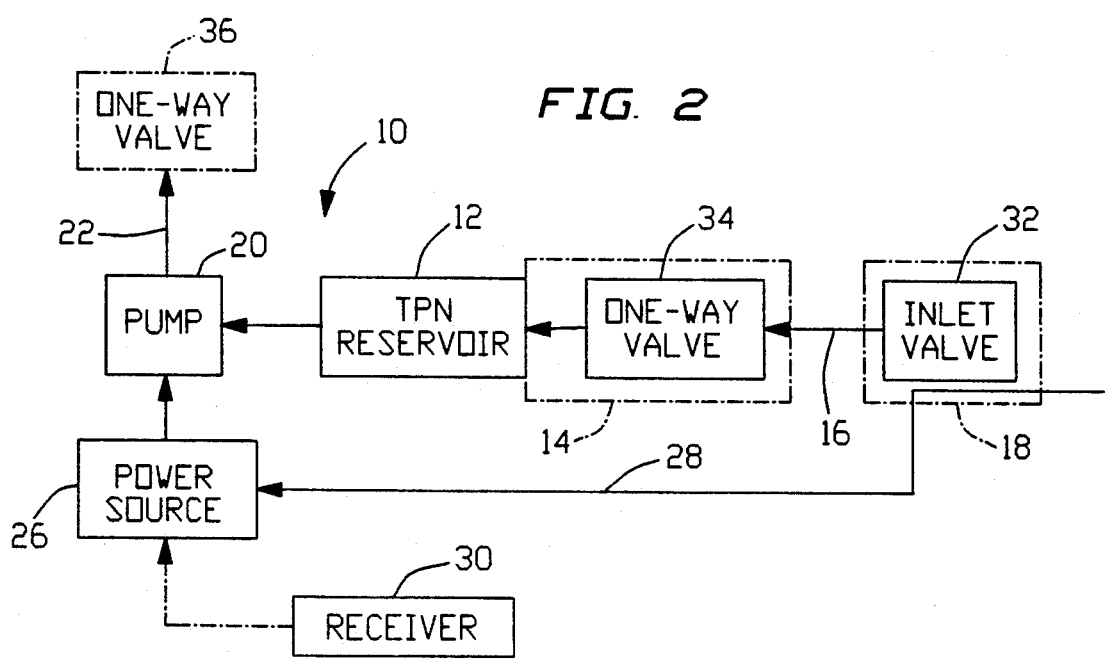
FIG. 2 is a block diagram of operative components of the implanted nutrition reservoir assembly of FIG. 1.

As illustrated in FIG. 2, container 12 is provided with a power source 26 operatively connected to pump 20 for energizing the pump. Power source 26 may be periodically energized or charged from a power supply (not shown) outside the patient's body. The charging of power source 26 may be effectuated by connecting power source 26 to the external power supply via a lead 28 extending through the abdominal wall AW of the patient. More particularly, lead 28 extends to port component 18 where an electrical contact may be formed. Alternatively, pump 20 is connected to a wireless energy receiver 30 which is attached to container 12 and which functions to extract power from an incoming wireless beam of electromagnetic or magnetic radiation.

Upon completion of implantation, the user or patient may periodically connect port component 18 to an external supply of a liquid nutrient for purposes of replenishing the supply in reservoir or container 12. Upon a disconnection of the external supply from port component 18, the port component is closed (e.g., with a cap, not illustrated). Upon the filling of container 12, an amount of the nutritive composition is continuously or periodically pumped by pump 20 from container 12 to the patient's liver LV via the portal vein system PVS.

As further illustrated in FIG. 2, the total parenteral nutrition assembly 10 further includes an inlet valve 32 at port component 18 and another one-way valve 34 at inlet port 14. A one-way valve 36 may additionally be provided in the output line extending to the portal vein system PVS.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A medical method for providing nutrition to a patient, comprising the steps of:
   providing a container having an inlet, an outlet and a pump at said outlet;
   surgically inserting said container into the abdominal cavity of the patient;
   surgically connecting said outlet to a selected vein in the portal vein system so that said container communicates with the liver via said outlet and the selected vein of the portal vein system; and
   operating said pump to move a liquid nutritive composition from said container to the selected vein in the portal vein system.

2. The method defined in claim 1, further comprising the steps of providing a port in an abdominal wall of the patient and connecting said inlet to said port.

3. The method defined in claim 2, further comprising the step of feeding a supply of liquid nutritive composition to said container via said port and said inlet.

4. The method defined in claim 1 wherein said container is provided with a power source for energizing the pump, further comprising the step of charging said power source from a power supply outside the patient's body.

5. The method defined in claim 4 wherein said step of charging includes the step of connecting said power source to said power supply via a lead extending through the abdominal wall of the patient.

6. The method defined in claim 1 wherein said step of inserting includes the step of disposing said container to rest on the pelvic rim.

7. A method for obtaining nutrition, comprising the steps of:

connecting, to a port provided in a person's abdominal wall, a supply of a liquid nutritive composition;

moving said liquid nutritive composition from said supply through said port and through an inlet supply line in the abdominal cavity of the person to a reservoir surgically implanted in said abdominal cavity;

disconnecting said supply from said port;

closing said port upon disconnection of said supply therefrom; and automatically pumping an amount of said nutritive composition from said reservoir to a vein of the portal vein system.

8. The method defined in claim 7, further comprising the step of charging a power source attached to said reservoir, said step of pumping including the step of energizing a pump with power from said power source.

9. The method defined in claim 8 wherein said step of charging includes the step of connecting said power source to an electrical power supply outside of the person.

* * * * *

UNITED STATES PATENT AND TRADEMARK OFFICE
CERTIFICATE OF CORRECTION

PATENT NO. : 5,318,519
DATED : June 7, 1994
INVENTOR(S) : Peter J. Wilk

It is certified that error appears in the above-indentified patent and that said Letters Patent is hereby corrected as shown below:

Column 2, line 48, insert --in accordance with the present invention-- after "person".

Column 3, line 16, change "16" to --22--; line 46, change "16" to --22--; line 49, change "16" to --22--; line 52, change "16" (first occurrence) to --22--; line 52, change "16" (second occurrence) to --12--; line 54, change "parental" to --parenteral--; line 61, change "all" to --wall--.

Column 4, line 3, change "14" to --12--.

Signed and Sealed this

Thirtieth Day of May, 1995

*Attest:*

BRUCE LEHMAN

*Attesting Officer*     *Commissioner of Patents and Trademarks*